(12) United States Patent
Papandreou et al.

(10) Patent No.: US 6,171,232 B1
(45) Date of Patent: *Jan. 9, 2001

(54) METHOD FOR TARGETING IN VIVO NITRIC OXIDE RELEASE

(75) Inventors: George Papandreou, Miami; Pallassana V. Narayanan, Davie, both of FL (US)

(73) Assignee: Cordis Corporation, Miami, FL (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/882,880

(22) Filed: Jun. 26, 1997

(51) Int. Cl.$^7$ ................................. A61F 2/04; A61F 2/06
(52) U.S. Cl. ..................... 600/36; 623/1.42; 623/1.46; 623/901; 427/2.25; 424/423
(58) Field of Search ................. 623/1, 11, 1.42, 623/1.46, 1.48, 901, 902, 903; 427/2.25; 424/423; 600/36

(56) References Cited

U.S. PATENT DOCUMENTS

| | | |
|---|---|---|
| 5,132,108 | 7/1992 | Narayanan et al. . |
| 5,171,217 | * 12/1992 | Morch et al. ............... 128/898 |
| 5,244,654 | 9/1993 | Narayanan . |
| 5,336,518 | 8/1994 | Narayanan et al. . |
| 5,409,696 | 4/1995 | Narayanan et al. . |
| 5,443,955 | * 8/1995 | Cornell et al. ............... 435/7.21 |
| 5,676,963 | * 10/1997 | Keefer et al. ............... 424/423 |
| 5,797,887 | * 8/1998 | Rosen et al. ............... 623/1.46 |

OTHER PUBLICATIONS

Hackh's Chemical Dictionary, Fourth Edition, McGraw-Hill Books Company, (1969), pp. 22 and 36.*
Epstein, "The New Miracle Drug May Be—Smog?", Science & Technology, pp. 108–109, Dec. 5, 1994.
Welch, et al., "Nitric Oxide as a Vascular Modulator", Circulation, vol. 87, pp. 1461–1467.
Anderson, et al., "Nitric Oxide and Nitrovasodilators: Similarities, Differences and Potential Interactions", Journal of American College of Cardiology, vol. 24, pp. 555–556, Aug., 1994.
Hawley's Condensed Chemical Dictionary, Eleventh Edition, Van Nostrand Reinhold (1987), pp. 31 and 341.
Stamler et al., "S–Nitrosylation of proteins with nitric oxide: Synthesis and characterization of biologically active compounds", Proc. Natl. Acad. Sci. USA, vol 89, pp. 444–448, Jan. 1992.
David S. Marks et al., "Inhibition of Neointimal Proliferation in Robbits after Vascular Injury by a Single Treatment with a Protein Adduct of Nitric Oxide", J. Clin. Invest., vol. 96, Dec. 1995.
Ewing et al., "Nitrosylated Bovine Serum Albumin Derivatives as Pharmacologically Active Nitric Oxide Congeners", J. Pharmacology and Experimental Therapeutics, vol. 283, Issue 2, pp. 947–954, 1997.

* cited by examiner

Primary Examiner—Paul B. Prebilic
(74) Attorney, Agent, or Firm—Cook, Alex, McFarron, Manzo, Cummings & Mehler, Ltd.

(57) ABSTRACT

The preparation and use of medical devices are described. A thiol group agent is loaded onto a medical device such as a stent or a catheter. Preferably, the loading is accomplished onto a polymeric surface that had been activated by water vapor RF plasma treatment. The thiol group agent is structured to exhibit sulfhydryl groups. These sulfhydryl groups are available for interaction with NO carriers such as nitrovasodilators. This interaction can take place in situ at an in vivo location within a vascular system, for example, in which event the sulfhydryl groups would be delivered by the medical device while the NO carrier will be delivered by suitable pharmaceutical administration means. Alternatively, the NO carrier can be loaded onto the treated medical device surface at a suitable time prior to insertion of the medical device into the body, such as immediately before the initiation of a medical procedure such as stent delivery and implantation.

25 Claims, 1 Drawing Sheet

METHOD FOR TARGETING IN VIVO NITRIC OXIDE RELEASE

BACKGROUND OF THE INVENTION

This invention generally relates to coated medical devices and to procedures for coating and administering same. More particularly, a thiol group containing agent is loaded onto a medical device for in vivo interaction with a nitric oxide donor. In the illustrated preferred embodiment, protected sulfur containing compounds are covalently attached onto medical device surfaces of polymer-coated metals, polymers and the like. These thus immobilized compounds, when deprotected, present sulfhydryl groups which are useful for enhancing local release of nitric oxide in vivo, or at the site of an implanted medical device and the like, when a nitric oxide donor such as a vasodilator is administered. Such nitric oxide release is of value, for example, in preventing platelet aggregation and smooth muscle cell proliferation. Possible thrombosis and/or restenosis which might be associated with the device implant is thereby minimized or even eliminated.

The liberation of nitric oxide from vasodilators, particularly nitric oxide donors, is generally believed to be potentiated by thiol donors. To the extent that thiol group containing agents are efficacious with respect to nitric oxide release, such can enhance the effectiveness of a nitric oxide containing agent or compound. It is accordingly believed that the effectiveness of vasodilators can be enhanced by their interaction with compounds which contain thiol groups. Observations made in this regard are discussed in Anderson, et al., "Nitric Oxide and Nitrovasodilators: Similarities, Differences and Potential Interactions", *Journal American College of Cardiology*, Vol. 24, pages 555–566, August, 1994, and in Welch, et al., "Nitric Oxide as a Vascular Modulator", *Circulation*, Vol. 87, pages 1461–1467, 1993, both incorporated hereinto by reference.

Concerns with respect to clinical and interventional procedures, including those involving vascular implants for example, include stenosis development or restenosis over time. In this regard, endoprostheses such as stents, catheters or any other device which is contacted by blood during a clinical or interventional procedure in the vascular system, run the risk of stenosis development. For example, a stent which had been implanted in order to address a stenosis situation would be much more desirable and efficacious if the stent itself discouraged stenosis at the implantation site.

Accordingly, approaches are needed which will directly address stenosis and restenosis concerns with respect to vascular implants. For example, it can be important to prevent smooth muscle cell proliferation, which has been associated with restenosis. Also to be prevented is platelet aggregation and its attendant thrombosis development.

Biocompatibility enhancement of vascular implants such as stents and the like can include coating treatment approaches. An example in this regard is Narayanan et al U.S. Pat. No. 5,336,518, incorporated by reference hereinto. With this technology, bioactive agents are secured to a metal surface of a medical device by an approach which includes treating a metal surface having a polymeric coating with water vapor plasma in order to facilitate attachment of the biologically active agent to the polymer coating. Various biologically active agents are discussed, including numerous agents such as the heparins and vasodilators.

SUMMARY OF THE INVENTION

In accordance with the present invention, important advances in the efficacy of vascular devices and implants can be facilitated. More particularly, it has been determined that compounds having thiol groups can be loaded onto an implant, intervention tool or other medical device for use in the vascular system. One such loading procedure couples a protected sulfur compound to the surface of the endoprosthesis, interventional tool or other medical device by bonding same to reactive groups formed on a polymeric surface of the device. The sulfurs are protected in an thio form of the compound and are deprotected thiol groups prior to implantation or use. Such surface thiol group moieties, when implanted, will be positioned at a location at which it is desired to retard or eliminate stenosis development or achieve other benefits as generally discussed herein and in the publications incorporated by reference. When a nitrovasodilator is administered to the patient and/or loaded onto the treated device, the nitrovasodilator has the opportunity to directly contact the compound having the thiol group properties as discussed. This contact is particularly advantageous because it is at the location at which stenosis and restenosis can be advantageously addressed. This interaction between a nitrovasodilator and the thiol groups has the opportunity to release nitric oxide and experience the benefits associated with it, including retarding or preventing platelet aggregation and smooth muscle cell proliferation. By having the desired coating on the device itself, the nitric oxide release is locally targeted. Stenosis or restenosis is thus addressed locally.

It is accordingly a general object of the present invention to provide improved procedures, coatings and medical devices for enhancing local nitric oxide release.

Another object of this invention is to provide improved procedures, coatings and medical devices for at least minimizing and substantially retarding restenosis of a medical device after its implantation within the vascular system.

Another object of the present invention is to provide improved medical devices having chemical compounds loaded thereon for enhancing the effectiveness of nitrovasodilators when they are administered to patients having endoprostheses or other devices implanted within the vascular system of the patient.

Another object of this invention is the improvement of medical devices, coatings and procedures relating to minimizing or eliminating restenosis through the use of carbodiimide chemistry in attaching compounds with operative groups to work with nitrovasodilators in accelerating release of nitric oxide at a specific location within the body.

A further object of the present invention is to provide medical devices having sulfhydryl groups on their working or engagement surfaces to provide the favorable property of accelerating release of nitric oxide locally when patients within which the medical devices are implanted are administered nitrovasodilators such as nitroglycerin.

Another object of the present invention is to provide an improved stent which has been treated so as to address possible restenosis when the patient within which the stent is implanted is administered a nitrovasodilator.

These and other objects, features and advantages of the present invention will be apparent from and clearly understood through a consideration of the following detailed description.

BRIEF DESCRIPTION OF THE DRAWINGS

In the course of this description, reference will be made to the attached drawings, wherein.

DESCRIPTION OF THE PREFERRED EMBODIMENTS

The present invention is particularly well suited for improving stenosis resistance at locations at which medical devices are implanted. The invention is especially useful for devices which include metallic surfaces, although it is also applicable to medical devices having polymeric surfaces. Special application is found with respect to stents or other endoprostheses which are to be deployed within the vascular system. Use on distal portions of catheters and the like is also possible.

Figure 1:
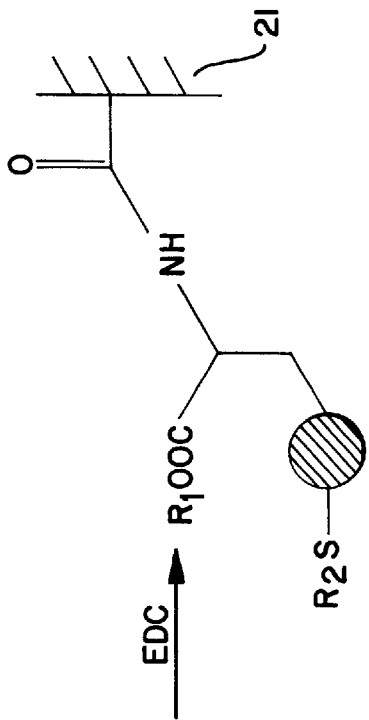
FIG. 1 is a schematic representation of one chemical reaction scheme for attaching a protected thiol group compound to a medical device.
Figure 1:
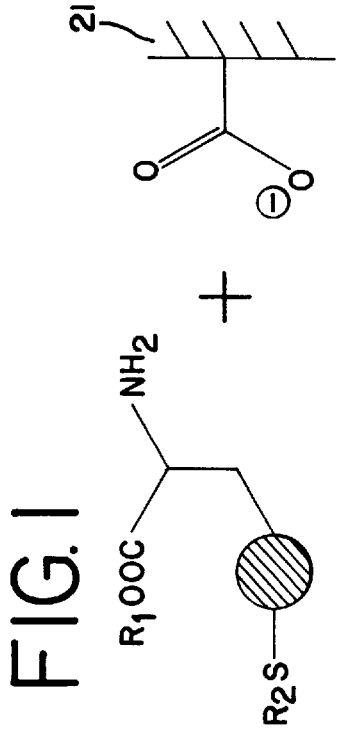

In one embodiment, which is generally illustrated in FIG. 1, a surface 21, which will typically be metallic, is coated with a polymer. More specifically, a monomer is subjected to radiofrequency (RF) plasma deposition whereby the resulting polymer is attached to the surface 21. Typical monomers in this regard are ethylene, heptafluorobutyl methacrylate, methacrylic acid and the like. After this step, the surface is coated with a film of the resulting polymer, for example polyethylene or poly(heptafluorobutyl methacrylate). This polymer film is functionalized by water vapor RF plasma treatment, typically after the initial plasma deposition has proceeded or has been substantially completed. The functionalization provides reactive carboxy and/or hydroxy groups, as generally illustrated in FIG. 1.

The thus surface activated polymer-coated metal is, in accordance with this particular chemical reaction scheme, ready for chemical attachment of a compound which has a protected sulfur moiety. In addition, such a compound also includes an amine group. The amine group, which is typically a primary amine or a secondary amine, forms a covalent bond with the activated polymer. This is illustrated in FIG. 1 as a reaction between the amine group and the carboxy group of the activated polymer.

This reaction typically proceeds by a condensation reaction or peptide bond formation using a carbodiimide coupling agent. The result is formation of a covalent bond between the carboxy groups of the activated polymer and the amine of the protected sulfur compound. More particularly, this coupling reaction can be carried out in the presence of 1-ethyl-3-dimethylaminopropyl carbodiimide (known as EDC) as a coupling agent.

Although carbodiimide chemistry is one mechanism by which the activated polymer and the protected sulfur compound are covalently bonded, different reaction schemes and reagents will also produce the desired result. Such schemes and reagents include, without limitation, organosilane chemistry, photoreactive crosslinkers, acid halide or epoxide chemistry, reductive amination as well as glutaraldehyde cross-linking.

While the protected sulfur compound may be applied directly to the activated polymeric surface as illustrated in FIG. 1, it may at times be desirable to first attach a spacer group prior to treating the surface with the protected sulfur compound. Suitable spacer groups include albumin, polyethyleneimine, polyethylene glycol and N-(2-aminoethyl-3-aminopropyl) trimethoxysilane. Where the protected sulfur compound is bound through an organosilane spacer molecule, the reaction is a condensation reaction between the hydroxy groups on the polymeric surface and the silane functionality on the organosilane. The protected thiol group compound is subsequently bound to the amine of the silane by carbodiimide chemistry.

Although not specifically illustrated in FIG. 1, a subsequent step is the deprotection to the sulfur group. For example, the $R_2S$ protected sulfur group is deprotected to an SH group by suitable chemistry as discussed herein. This sulfhydryl group is then available on the surface of the medical device for positively affecting a nitrovasodilator. More specifically, the sulfhydryl group interacts with the nitrovasodilator so as to facilitate the release of nitric oxide (NO). This release is most advantageously effected at the location of the medical device. Thus, when this approach is followed in connection with a stent or a distal portion of a catheter, the sulfhydryl groups thereon interact with the nitrovasodilator which is administered to be at the location of the medical device. This results in in situ release of NO from the nitrovasodilator by the influence of the sulfhydryl groups. This is accomplished under in vivo conditions. As a result, the NO is formed and delivered directly at the site at which its advantageous effects are most efficiently utilized.

Figure 2:
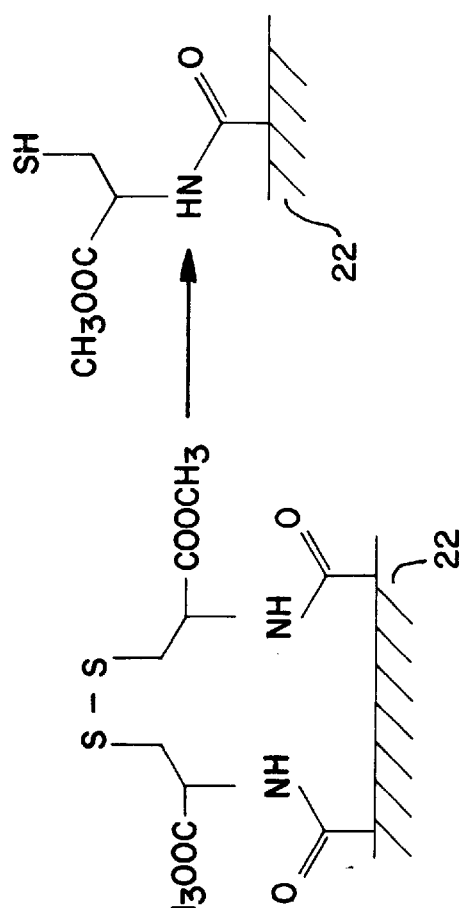
FIG. 2 is a schematic representation of another chemical reaction scheme by which a thiol-protected compound is immobilized on a surface of a medical device such as a stent and then deprotected to expose a reactive sulfhydryl group.
Figure 2:
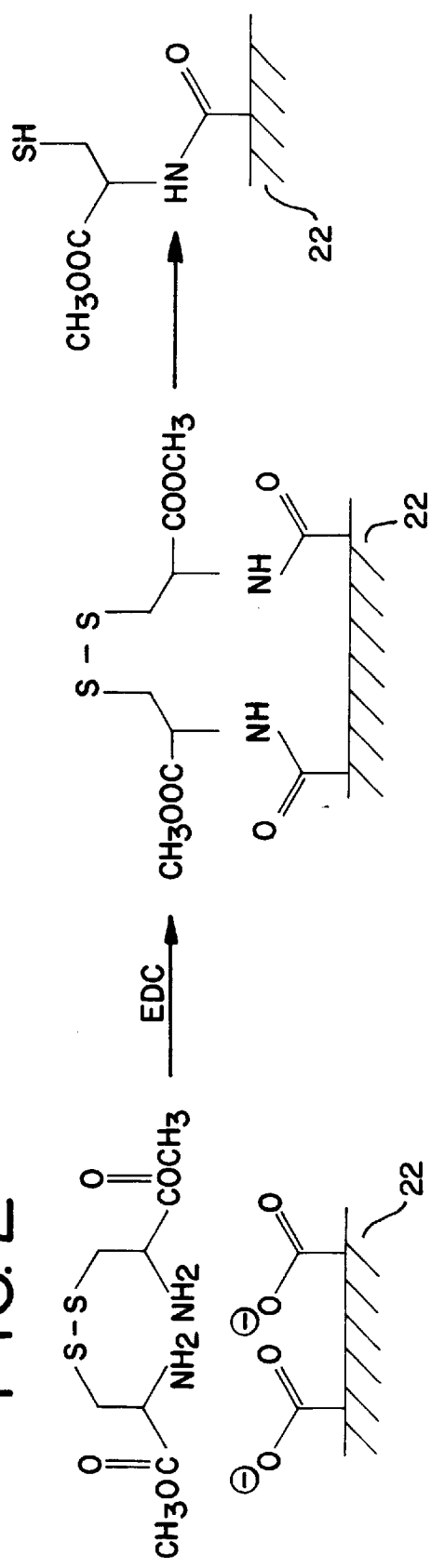

With reference to the chemical reaction scheme illustrated in FIG. 2, the primary difference between it and the FIG. 1 reaction scheme is the mechanism by which the sulfur atom is protected. The utilization of an S—S bridge is practiced in the reaction scheme of FIG. 2. A sulfur-sulfur bridge is formed by a dimerization reaction, or a compound already containing an S—S bridge is provided. Either way, the —S—S— protected sulfur compound is covalently attached, such as through its amine groups as illustrated, to the activated polymeric surface 22.

As with the reaction scheme illustrated in FIG. 1, this FIG. 2 chemical reaction scheme typically proceeds by a condensation reaction or peptide bond formation using a carbodiimide coupling agent. The result is formation of a covalent bond between the activated carboxy groups of the polymer and the amine groups of the protected thiol group compound. Typically, this coupling reaction will be carried out in the presence of EDC as a coupling agent.

Prior to implantation or insertion under in vivo conditions, the S—S bond is broken, and sulfhydryl groups are formed. Once the working surface of the medical device is at its treatment location, it is in a position and state to interact with a nitrovasodilator. This thiol donor action releases nitric oxide for achieving the beneficial effects as discussed herein.

The chemical reaction schemes of FIG. 1 and of FIG. 2 illustrate embodiments wherein the protected sulfur compound is covalently attached to a plasma activated polymeric surface which had been deposited onto a metallic surface of the medical device being modified in accordance with the invention. When the portion of the medical device which is to be modified in accordance with the present invention is not metallic, then it is not required to coat a metallic surface with a polymer, such as through the RF plasma polymerization of monomers onto the metal surface. Instead, the polymeric surface of the medical device can be activated with the water vapor RF plasma as discussed herein. Typical polymers which are susceptible to this activation technique include various polyurethane-containing polymers including polyurethanes and polyurethane copolymers, such as Pellethane polymers. Included are polyurethane-polyester copolymers, polyurethane-polyether copolymers and nylon-polyether copolymers, such as Vestamid. Other polymers in this regard include silastic (silicon rubber), nylons and other polyamides, nylon-polyester copolymers, polyolefins such as high density polyethylene and the like. The selected polymer must have overall properties which otherwise render the polymers suitable for use on medical devices. To the extent necessary, polymers such as these can be RF plasma polymerized onto the surface of other polymers, as well as onto metallic surfaces.

In an important embodiment, the nitric oxide donor or provider is delivered to the treatment location by any of several different approaches. These include oral ingestion, intravenous feeding, direct injection, patch attachment to an external body location, and loading onto the medical device prior to its implantation or insertion, such as immediately before the device is inserted during the medical procedure.

With respect to the components exhibiting protected sulfur atoms which can be suitably deprotected in order to provide the sulfhydryl group for interaction with the NO carrier components, these include the following. Compounds capable of undergoing S—S bridge formation and subsequent cleavage of the S—S bridge structure can be generally characterized as disulfides. The particular disulfide illustrated in the reaction scheme of FIG. 2 is cystine dimethylester. After deprotection, cysteine methylester is shown. Other disulfides include cystine diethylester and its corresponding non-dimerized cysteine ethylester. Other molecules containing thiols which could be produced in the protected sulfur form include the following and their derivatives: S-nitroso-L-cysteine, N-acetylcysteine, and glutathione, which contains glutamic acid, cysteine and glycine. Cysteine and cystine per se are generally believed to be less desirable because they include unprotected carboxy groups. In this regard, it will be appreciated that cysteine, depending upon the nomenclature used, is also known as alpha-amino-beta-thiolpropionic acid or as beta-mercaptoalanine. Similarly, cystine in accordance with other nomenclature is known as beta,beta'-dithiobisalanine, or di[alpha-amino-beta-thiolpropionic acid], or dicysteine, or 3,3'-dithiobis(2-aminopropanoic acid). Other examples of protectable thiol-containing compounds include thiosalicylic acid, otherwise identified as 2-thiolbenzoic acid, or 2-mercaptobenzoic acid, or sulfhydryl benzoic acid, and also captropril, or 1-(3-mercapto-2-methyl-1-oxypropyl)-L-proline. See, for example, *Protective Groups in Organic Synthesis*, Greene, T. W., Ed., Wiley, New York 1981, and *The Chemistry of the Thiol Group*, Patai, S., Ed., Wiley, New York 1974, incorporated hereinto by reference.

Concerning non-disulfide components suitable for use in connection with the invention, these can fall within the categories of thioethers, thioesters and semithioacetals. It will be appreciated that these components would be used in a reaction scheme such as shown in FIG. 1.

Suitable thioethers include dinitrophenyl thioethers. For example, a protected dinitrophenyl thioether is prepared by reacting RSH with a dinitrophenyl halide compound. After attachment of the protected thioether to the medical device surface, deprotection or removal of the R group to form the SH group can be accomplished by the use of mercaptoethanol, typically at pH=8. Diphenylmethylthioethers can be provided in protected form by reacting RSH with $Ph_2CH$—$OH+BF_3.OEt_2$, with removal or deprotection being accomplished through the use of $CF_3COOH$. Triphenylmethylthioethers can be provided in protected form by combining RSH and $Ph_3C$—Cl, with deprotection or removal being accomplished through the use of $I_2$ or EtSH, $CF_3COOH$. $I_2$ can also be used for removal or deprotection of acetamidomethyl thioethers of the structure

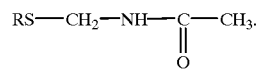

With reference to thioesters capable of providing intermediate protected sulfur groups, examples of protected intermediates include acetate thioesters,

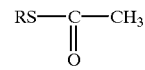

and benzoate thioesters,

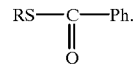

Removal of the ester group from such protected intermediates can be accomplished by the use of dilute sodium hydroxide, or the by use of NaOMe/MeOH. Ethylcarbamoyl thioesters in the intermediate protected form are included, such as

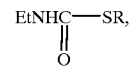

with removal of the protecting group and formation of the SH group being accomplished by dilute sodium hydroxide as the deprotection agent.

Regarding the semithioacetals, examples include tetrahydropyranyl derivatives. The intermediate, protected form combines a tetrahydropyranyl moiety with RSH, and deprotection is obtained with dilute acid, $I_2$ or silver nitrate.

Various nitric oxide carriers are available for interaction with the deprotected thiol group donors. They are generally defined herein as nitrovasodilators having the property of acting as an exogenous source of nitric oxide, thereby exhibiting many of the same attributes as nitric oxide. Included are organic nitrates, perhaps the most recognizable of these being nitroglycerine, or glycerol trinitrate. Also included are isosorbide dinitrate and isosorbide 5-mononitrate. These components and sodium nitroprusside are generally approved nitric oxide donor pharmaceuticals. Other organic nitrates which are at the present time within the category of experimental pharmaceuticals include diazoniumdiolate derivatives (polyamines containing the $N_2O_2$— group; see U.S. Pat. No. 5,155,137, incorporated hereinto by reference) and N- and S-nitroso-serum albumin. Other nitric oxide carriers include sodium nitrite, isoamyl nitrite, isopropyl nitrite, Tempo and the Sydnonimines, for example, molsidomine and its active metabolite.

With further reference to the procedure discussed generally herein, the polymeric medical device surface or the polymer coating or the metallic medical device surface is activated using an RF water vapor plasma treatment. The plasma medium is preferably nominally all water vapor, it being appreciated that low levels of oxygen or air can remain and be tolerated in a water vapor plasma. For example, the medical device can be mounted within a long glass reactor tube which is RF coupled capacitively by external electrodes. The system is pumped down to remove air or other residual gases. Water vapor is introduced into the reactor while the pressure is controlled at about 400 mTorr, and RF power is applied to create the water vapor plasma. This condition is carried out for about one minute in order to modify the polymer surface of the medical device.

This activated surface is then treated with the chosen protected sulfur material or with a spacer molecule as discussed herein. Typically, this is carried out in the presence of a carbodiimide to facilitate condensation or peptide bond formation. As a coupling agent, the carbodiimide will activate the carboxy group on the polymer for coupling with the amine or other reactive group on the spacer molecule or the protected sulfur component. Generally, an equal weight ratio of EDC and the thiol-containing component will approximate the levels required. Typically, this reaction will take place at a slightly acidic pH, for example between pH3 and about pH7. It will be appreciated that the specific reaction conditions will vary considerably depending upon the particular components being used. It will also be appreciated that a carbodiimide is not necessarily required with certain spacer molecules such as an organosilane spacer group inasmuch as a condensation reaction will occur between the activated polymeric surface and hydroxy groups of the silane functionality.

Exemplary illustrations of the disclosure herein are provided in the following examples.

EXAMPLE 1

A heptafluorobutyl methacrylate coating is placed upon a metallic endoprosthesis by RF plasma polymerization using volatile heptafluorobutyl methacrylate. Carboxyl and hydroxyl groups are then introduced onto this polymer surface by a nominal 100% water vapor RF plasma treatment. To this polymer coating, polyethylene imine is attached, using a solution of polyethylene imine in water at pH=6–9 and EDC to couple some of the amino groups of the polyethylene imine to the carboxyl groups of the polymer. Commercially available S-acetylthioglycolic acid N-hydroxysuccinimide ester is then immobilized on the polymer surface. This coupling is performed using EDC chemistry to bind primary and second amino groups of the polyethylene imine spacer to the N-hydroxysuccinimido activated carboxyl group of thioglycolic acid. The attached immobilized thioglycolic acid is then deprotected in order to generate sulfhydryl groups. The medical device is then implanted within a living body, and nitroglycerin is administered by oral dosage. The nitroglycerin flows through the bloodstream and encounters particularly favorable conditions for release of nitric oxide when same engages the treated medical device at the implantation site. Nitric oxide has been indicated as being efficacious for preventing platelet aggregation and smooth muscle cell proliferation.

EXAMPLE 2

Tantalum foil was coated by RF plasma deposition of heptafluorobutyl methacrylate and subsequently modified using water vapor RF plasma. Using the reaction scheme of FIG. 2, cystine dimethylester was immobilized on the thus treated tantalum foil. The protected cystine was immobilized by way of an amide linkage, after surface activation with EDC. The immobilization was confirmed by x-ray photoelectron spectroscopy, which detected the sulfur from the immobilized cystine. The deprotection of the sulfhydryl group was performed with disulfide bond cleaving reagents, such as dithiothreitol (DTT).

EXAMPLE 3

Four tantalum foil sheets were coated with cystine dimethylester at a concentration of 5 mg/ml in deionized water. These sheets were activated with 5 mg/ml of EDC for 30 minutes, the foils having been HP coated and water functionalized as discussed herein. The sheets were rinsed with deionized water. Two sheets were placed in a clean container and extracted with phosphate buffered saline at 37° C. for one hour.

The thus prepared sheets were subjected to XPS analysis (a surface-specific, semi-quantitative elemental analysis method). In the sample which was not rinsed with PBS, the XPS analysis confirmed the presence of sulfur. A sample which was rinsed with PBS still contained sulfur, as indicated by the elemental analysis.

EXAMPLE 4

Tantalum sheets were RF plasma coated with heptafluorobutyl methacrylate (HP) plasma. Sheets thus prepared were soaked in 5 mg/ml EDC solution for 30 minutes. Each was then placed into a deionized water solution of L-cystine dimethylester dihydrochloride solution at 5 mg/ml. Soaking proceeded for one hour, followed by rinsing. A 0.770 mg/ml solution of dithiothreitol (DTT) in deionized water was poured on half of the thus treated sheets and allowed to soak for approximately two hours, followed by rinsing.

EXAMPLE 5

A number of tantalum foils were RF plasma treated with heptafluorobutyl methacrylate and activated with water plasma. Some of these foils were soaked in 5 mg/ml of EDC solution for one hour at room temperature. Following activation, the foils were subjected to a 5 mg/ml solution of L-cystine dimethylester for two hours at a pH of about 5.

After treatment with a 50 mM solution of dithiothreitol (DTT), the thiol containing foils were reacted with isopropyl nitrite or isoamyl nitrate. After thorough rinsing with saline to remove unbound organic nitrite, inorganic nitrite, or free nitrosothiol, the foils were dropped into a chamber containing phosphoric acid and potassium iodide. The resulting reaction $2HI+2RSNO=RSSR +I_2+2NO$ converts all nitrosothiols to NO. The headspace of the chamber was continuously drawn into a chemiluminescence NO analyzer. This analysis provided 1038±408 picomoles of $NO/cm^2$ of metal.

EXAMPLE 6

Twelve coronary stents having an activated polymeric surface were coated with PEI, pH approximately 9, for 30 minutes. After rinsing, the stents were immersed in N,N-bis-(t-BOC)-L-cystine in the presence of EDC for two hours at room temperature. Another twelve stents having an activated polymeric surface were soaked in L-cystine dimethylester and EDC for two hours. The stents were rinsed with water. Six of the coated stents in each group were treated with DTT for two hours at room temperature.

The presence of free sulfhydryl groups after DTT treatment was verified with 5,5'dithiobis(2-nitro-benzoic acid)(or DTNB, Ellman's reagent). Stents at the disulfide stage (—S—S—, before DTT treatment) and the cysteine stage (—SH, after DTT treatment) were incubated with the DTNB solution. After one hour, the solution was spectroscopically measured at 395–420 nm, and the presence of the degradation product, generated by free thiol groups, 5-thio,2-nitrobenzoic acid, was monitored by an increase in adsorption.

The presence of free thiol groups was indeed confirmed with the DTNB assay. The absorbance of the assay mixture was significantly higher for the six coated stents, which were subjected to the DTT deprotection step, as compared to the stents not subjected to DTT treatment. The generation of —SH groups by DTT from the L-cystine dimethylester samples was more pronounced than —SH group production from t-BOC-L-cystine coated samples.

EXAMPLE 7

Ten coronary stents were exposed to 25% PEI at pH9 for thirty minutes, followed by rinsing with deionized water. A 5 mg/ml solution of T-BOC cystine hydrochloride was activated for 60 minutes with 5 mg/ml EDC, the solution being prepared using 50–50% water-ethyl alcohol. After this activation, the 10 previously PEI-coated stents were exposed to this solution at room temperature for two hours. These stents were rinsed. After storage for about six weeks in a vial, half of the stents were subjected to the DTNB assay for —SH group detection.

EXAMPLE 8

Ten stents having an activated polymeric surface were treated with a solution of 10 mg/ml L-cystine dimethylester hydrochloride in deionized water. The solution was activated for five minutes with 5 mg/ml EDC. The stents were exposed to this treatment for two hours. Each stent was rinsed with deionized water and stored in a vial. Approximately six weeks later, the stents were subjected to the DTNB assay for —SH group detection.

It will be understood that the embodiments of the present invention which have been described are illustrative of some of the applications of the principles of the present invention. Numerous modifications may be made by those skilled in the art without departing from the true spirit and scope of the invention.

What is claimed is:

1. A method of providing a medical device having a working surface for deployment within a vascular system, which comprises:

attaching a thiol group sulfur agent to a working surface of a medical device, said thiol group sulfur agent including a protected sulfur, said thiol group sulfur agent is selected from the group consisting of disulfides, thioethers, thioesters and semithioacetals;

deprotecting said protected sulfur with a removal agent while attached onto the working surface of the medical device to provide a treated working surface, said treated working surface having deprotected sulfhydryl groups;

loading a nitric oxide carrier onto said treated working surface having deprotected sulfhydryl groups; and interacting the nitric oxide carrier and sulfhydryl groups with each other to enhance the efficacy of the nitric oxide carrier.

2. The method according to claim 1, further including subjecting the working surface of the medical device to RF plasma activation prior to said attaching of the thiol group sulfur agent, said working surface being a polymeric surface.

3. The method in accordance with claim 1, wherein said working surface of the medical device is a metallic member having a polymeric coating thereon.

4. The method in accordance with claim 3, further including applying the polymeric coating by RF plasma deposition of a monomer which forms said polymeric coating.

5. The method in accordance with claim 1, wherein the nitric oxide carrier of the interacting procedure is a nitrovasodilator at said treated working surface having deprotected sulfhydryl groups.

6. The method in accordance with claim 1, wherein said thiol group sulfur agent has an RS group having the protected sulfur.

7. The method in accordance with claim 1, wherein said thiol group sulfur agent has an S—S bridged chemical structure having the protected sulfur.

8. The method in accordance with claim 1, wherein said thiol group sulfur agent is a cystine compound, and said deprotected sulfur agent is a cysteine compound.

9. The method in accordance with claim 5, wherein the nitrovasodilator of the interacting procedure is nitroglycerine.

10. A process of interacting a treated medical device and a nitric oxide carrier, which process comprises:

loading a protected sulfur compound onto a medical device to provide same with a treated working surface, said protected sulfur compound being selected from the group consisting of disulfides, thioethers, thioesters and semithioacetals;

deprotecting said protected sulfur compound upon contact with a removal agent while loaded onto the working surface of the medical device to provide a deprotected sulfur compound having deprotected sulfhydryl groups which are thus carried on said working surface of the medical device; and contacting a nitric oxide carrier with the deprotected sulfhydryl groups of the deprotected sulfur compound in order to interact with the deprotected sulfhydryl groups to thereby release NO in an in vivo environment within a body vessel.

11. The process in accordance with claim 10, wherein the nitric oxide carrier and the deprotected sulfur compound having deprotected sulfhydryl groups interact in situ.

12. The process in accordance with claim 10, further including subjecting the working surface of the medical device to RF plasma activation prior to attachment of the protected sulfur compound, the working surface being a polymeric surface.

13. The process in accordance with claim 10, wherein said working surface of the medical device is a metallic member having a polymeric coating thereon.

14. The process in accordance with claim 13, further including applying the polymeric coating by RF plasma deposition of a monomer which forms said polymeric coating.

15. The process in accordance with claim 10, wherein said protected sulfur compound has an RS group having the protected sulfur.

16. The process in accordance with claim 10, wherein said protected sulfur compound has an S—S bridged chemical structure having the protected sulfur.

17. The process in accordance with claim 10, wherein said protected sulfur compound is a cystine compound, and said deprotected sulfur agent is a cysteine compound.

18. The process in accordance with claim 10, wherein the nitric oxide carrier of the contacting procedure is nitroglycerine.

19. A method for targeting in situ release of NO from an NO carrier, comprising the steps of:

providing a medical device having a surface suitable for being delivered in vivo to a treatment location within a living body;

loading a thiol group agent onto the surface of the medical device, said thiol group agent having an intermediate structure including a protected sulfur and a protecting agent;

contacting said thus loaded thiol group agent with a removal agent for the protecting agent to thereby deprotect the thiol group and provide a medical device having a thiol donor treatment surface;

inserting the medical device to position the thiol donor treatment surface at the in vivo treatment location;

delivering an NO carrier to the in vivo treatment location; and interacting said thiol donor treatment surface and said NO carrier with each other to effect release of NO from the NO carrier.

20. The method in accordance with claim 19, wherein said interacting step is carried out in situ at an in vivo treatment location.

21. The method in accordance with claim 19, wherein said interacting step is carried out prior to said inserting and delivering steps.

22. The method in accordance with claim 21, wherein said delivering step is initiated prior to initiation of said inserting step.

23. The method in accordance with claim 19, wherein said loading step includes covalently bonding the thiol group agent having the intermediate structure to the surface of the medical device.

24. The method in accordance with claim 23, further including subjecting the surface of the medical device to an RF plasma treatment to form an activated surface having carboxy and/or hydroxy groups thereon.

25. The method in accordance with claim 24, wherein said loading step further includes applying a spacer group compound onto the activated surface and reacting the spacer group compound with both the activated surface and the thiol group agent.

* * * * *

UNITED STATES PATENT AND TRADEMARK OFFICE
CERTIFICATE OF CORRECTION

PATENT NO. : 6,171,232 B1
DATED : January 9, 2001
INVENTOR(S) : Papandreou et al.

It is certified that error appears in the above-identified patent and that said Letters Patent is hereby corrected as shown below:

Column 1,
Line 1, "IN VIVO" should read -- IN VIVO --.
Line 8, "in vivo" should read -- in vivo --.
Line 14, "in vivo" should read -- in vivo --.

Column 2,
Line 8, after "in" an" insert -- intermediate --.
Line 9, after "deprotected" insert -- to --

Column 3,
Line 2, delete "thiol-protected" and insert -- protected thiol group --.

Column 4,
Line 16, "in situ" should read -- in situ --.
Line 18, "in vivo" should read -- in vivo --.
Linr 40, "in vivo" should read -- in vivo --.

Column 10,
Line 34, "in situ" should read -- in situ --.
Line 59, "in situ" should read -- in situ --.
Line 62 , "in vivo" should read -- in vivo --.

UNITED STATES PATENT AND TRADEMARK OFFICE
CERTIFICATE OF CORRECTION

PATENT NO. : 6,171,232 B1
DATED : January 9, 2001
INVENTOR(S) : Papandreou et al.

It is certified that error appears in the above-identified patent and that said Letters Patent is hereby corrected as shown below:

<u>Column 11</u>,
Line 6, "in vivo" should read -- *in vivo* --.
Line 7, "in vivo" should read -- *in vivo* --.
Line 13, "in situ" should read -- *in situ* --.
Line 13, "in vivo" should read -- *in vivo* --.

Signed and Sealed this

Eighth Day of January, 2002

*Attest:*

JAMES E. ROGAN
*Attesting Officer*  *Director of the United States Patent and Trademark Office*